US008106029B2

(12) United States Patent
Gordi et al.

(10) Patent No.: US 8,106,029 B2
(45) Date of Patent: *Jan. 31, 2012

(54) USE OF $A_{2A}$ ADENOSINE RECEPTOR AGONISTS

(75) Inventors: Toufigh Gordi, Sunnyvale, CA (US); Ann Walls Olmsted, Palo Alto, CA (US); Hsiao Dee Lieu, Burlingame, CA (US); Luiz Belardinelli, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/637,583

(22) Filed: Dec. 14, 2009

(65) Prior Publication Data

US 2010/0158797 A1    Jun. 24, 2010

Related U.S. Application Data

(63) Continuation of application No. 11/253,322, filed on Oct. 19, 2005, now Pat. No. 7,655,636.

(60) Provisional application No. 60/620,577, filed on Oct. 20, 2004.

(51) Int. Cl.
*A61K 31/70* (2006.01)
*C07H 19/167* (2006.01)

(52) U.S. Cl. ........................................ 514/46; 536/27.61
(58) Field of Classification Search .................... None
See application file for complete search history.

(56) References Cited

U.S. PATENT DOCUMENTS

| | | |
|---|---|---|
| 3,845,770 A | 11/1974 | Theeuwes et al. |
| 4,089,959 A | 5/1978 | Diamond |
| 4,120,947 A | 10/1978 | Diamond |
| 4,325,956 A | 4/1982 | Kjellin et al. |
| 4,326,525 A | 4/1982 | Swanson et al. |
| 4,593,095 A | 6/1986 | Snyder et al. |
| 4,696,932 A | 9/1987 | Jacobson et al. |
| 4,804,664 A | 2/1989 | Kjellin et al. |
| 4,902,514 A | 2/1990 | Barclay et al. |
| 4,956,345 A | 9/1990 | Miyasaka et al. |
| 4,968,697 A | 11/1990 | Hutchison |
| 4,992,445 A | 2/1991 | Lawter et al. |
| 5,001,139 A | 3/1991 | Lawter et al. |
| 5,032,252 A | 7/1991 | Owen et al. |
| 5,070,877 A | 12/1991 | Mohiuddin et al. |
| 5,189,027 A | 2/1993 | Miyasita et al. |
| 5,270,304 A | 12/1993 | Kogi et al. |
| 5,459,254 A | 10/1995 | Yamaguchi et al. |
| 5,516,894 A | 5/1996 | Reppert |
| 5,593,975 A | 1/1997 | Cristalli |
| 5,616,345 A | 4/1997 | Geoghegan et al. |
| 5,641,784 A | 6/1997 | Kufner-Muhl et al. |
| 5,646,156 A | 7/1997 | Jacobsen et al. |
| 5,670,498 A | 9/1997 | Suzuki et al. |
| 5,703,085 A | 12/1997 | Suzuki et al. |
| 5,704,491 A | 1/1998 | Graves |
| 5,705,491 A | 1/1998 | Yamada |
| 5,770,716 A | 6/1998 | Khan et al. |
| 5,776,960 A | 7/1998 | Oppong et al. |
| 5,780,481 A | 7/1998 | Jacobson et al. |
| 5,854,081 A | 12/1998 | Linden et al. |
| 5,877,180 A | 3/1999 | Linden et al. |
| 5,939,543 A | 8/1999 | Morozumi et al. |
| 6,026,317 A | 2/2000 | Verani |
| 6,117,878 A | 9/2000 | Linden |
| 6,214,807 B1 | 4/2001 | Zablocki et al. |
| 6,294,522 B1 | 9/2001 | Zablocki et al. |
| 6,322,771 B1 | 11/2001 | Linden et al. |
| 6,368,573 B1 | 4/2002 | Leung |
| 6,387,913 B1 | 5/2002 | Mustafa |
| 6,403,567 B1 | 6/2002 | Elzein et al. |
| 6,448,235 B1 | 9/2002 | Linden et al. |
| 6,514,949 B1 | 2/2003 | Linden et al. |
| 6,552,023 B2 | 4/2003 | Zablocki et al. |
| 6,599,283 B1 | 7/2003 | Marzilli et al. |
| 6,605,597 B1 | 8/2003 | Zablocki et al. |
| 6,642,210 B1 | 11/2003 | Zablocki et al. |
| 6,670,334 B2 | 12/2003 | Linden et al. |
| 6,677,336 B2 | 1/2004 | Zablocki et al. |
| 6,770,634 B1 | 8/2004 | Zablocki et al. |
| 6,825,349 B2 | 11/2004 | Kalla et al. |
| 6,855,818 B2 | 2/2005 | Zablocki et al. |
| 6,916,804 B2 | 7/2005 | Castelhano et al. |
| 6,977,300 B2 | 12/2005 | Kalla et al. |
| 6,995,148 B2 | 2/2006 | Jones et al. |
| 7,109,180 B2 | 9/2006 | Zablocki et al. |
| 7,109,203 B2 | 9/2006 | Hart et al. |
| 7,125,993 B2 | 10/2006 | Elzein et al. |
| 7,144,872 B2 | 12/2006 | Zablocki et al. |
| 7,183,264 B2 | 2/2007 | Zablocki et al. |
| 7,553,823 B2 | 6/2009 | Zablocki et al. |
| 7,582,617 B2 | 9/2009 | Belardinelli et al. |
| 7,655,636 B2 | 2/2010 | Gordi et al. |
| 7,655,637 B2 | 2/2010 | Zablocki et al. |
| 7,671,192 B2 | 3/2010 | Zablocki et al. |
| 7,683,037 B2 | 3/2010 | Belardinelli |

(Continued)

FOREIGN PATENT DOCUMENTS

CA    965411    4/1975

(Continued)

OTHER PUBLICATIONS

Bergmann et al., "Oxidation of Hypoxanthines, Bearing 8-Aryl or 8-Pyridyl Substituents, by Bovine Milk Xanthine Oxidase,", Biochimica et Biophysica Acta, vol. 484, No. 2, pp. 275-289 (1977).

(Continued)

*Primary Examiner* — Lawrence E Crane
(74) *Attorney, Agent, or Firm* — Foley & Lardner LLP

(57) ABSTRACT

Myocardial imaging methods are provided that are accomplished by administering doses of a pharmaceutical composition comprising one or more adenosine $A_{2A}$ receptor agonists, in particular regadenoson, useful for, among other indications, myocardial imaging and coronary vasodilation, in an amount sufficient to achieve at least a minimal increase in average coronary peak flow velocity.

15 Claims, No Drawings

U.S. PATENT DOCUMENTS

| | | |
|---|---|---|
| 2002/0012946 A1 | 1/2002 | Belardinelli et al. |
| 2003/0235555 A1 | 12/2003 | Shealey et al. |
| 2004/0137533 A1 | 7/2004 | Belardinelli et al. |
| 2005/0020915 A1 | 1/2005 | Belardinelli et al. |
| 2006/0159621 A1 | 7/2006 | Barrett |
| 2006/0159627 A1 | 7/2006 | Zeng et al. |
| 2007/0265445 A1 | 11/2007 | Zablocki et al. |
| 2007/0299089 A1 | 12/2007 | Belardinelli et al. |
| 2008/0170990 A1 | 7/2008 | Lieu et al. |
| 2008/0213165 A1 | 9/2008 | Lieu et al. |
| 2008/0267861 A1 | 10/2008 | Lieu et al. |
| 2009/0081120 A1 | 3/2009 | Lieu et al. |
| 2009/0317331 A1 | 12/2009 | Belardinelli et al. |
| 2010/0081810 A1 | 4/2010 | Zablocki et al. |
| 2010/0086483 A1 | 4/2010 | Belardinelli et al. |

FOREIGN PATENT DOCUMENTS

| | | |
|---|---|---|
| CA | 2064742 | 12/1991 |
| EP | 0 354 638 | 2/1990 |
| EP | 0 386 683 | 9/1990 |
| JP | SHO 48-26038 | 8/1973 |
| JP | HEI 5 1993 9197 | 1/1993 |
| WO | WO 92/00297 | 1/1992 |
| WO | WO 92/12260 | 7/1992 |
| WO | WO 93/23401 | 11/1993 |
| WO | WO 93/25677 | 12/1993 |
| WO | WO 95/11681 | 5/1995 |
| WO | WO 98/52611 | 11/1998 |
| WO | WO 98/57651 | 12/1998 |
| WO | WO 99/63938 | 12/1999 |
| WO | WO 00/78778 | 12/2000 |
| WO | WO 00/78779 | 12/2000 |
| WO | WO 01/16134 | 8/2001 |
| WO | WO 01/62979 | 8/2001 |
| WO | WO 03/088978 | 10/2003 |
| WO | WO 2004/011010 | 2/2004 |
| WO | WO 2005/082379 | 9/2005 |
| WO | WO 2006/076698 | 7/2006 |
| WO | WO 2007/092372 | 8/2007 |
| WO | WO 2008/028140 | 3/2008 |
| WO | WO 2008/042796 | 4/2008 |
| WO | WO 2008/063712 | 5/2008 |
| WO | WO 2008/086096 | 7/2008 |
| WO | WO 2008/143667 | 11/2008 |
| WO | WO 2006/044856 | 4/2009 |
| WO | WO 2009/076580 | 6/2009 |
| WO | WO 2010/037122 | 4/2010 |

OTHER PUBLICATIONS

Birdsall et al., "Purine N-Oxides-XL The 3-Acyloxypurine 8-Substitution Reaction: Scope: Syntheses of 8-Substituted Xanthines and Guanines," Tetrahedron, vol. 27, pp. 5969-5978 (1971).

Blackburn et al., "Adenosine Mediates IL-13-Induced Inflammation and Remodeling in the Lung and interacts in an IL13-Adenosine Amplification Pathway," J. Clin. Invest. vol. 112, No. 3, pp. 332-344 (2003).

Bruns, "Adenosine Antagonism by Purines, Pteridines and Benzopteridines in Human Fibroblasts," Biochemical Pharmacology, vol. 30, No. 4, pp. 325-333 (1981).

Buckle et al., "Inhibition of Cyclic Nucleotide Phosphodiesterase by Derivatives of 1,3-Bis(cyclopropylmethyl)xanthine," J. Med. Chem., vol. 37, pp. 476-485 (1994).

Cerqueira, "The Future of Pharmacologic Stress: Selective A2A Adenosine Receptor Agonists," Am. J. Cardiol., vol. 94 (2A), pp. 33D-42D (2004).

Cline et al., "Coronary Artery Angiography Using Multislice Computed Tomography Images," Circulation, vol. 102, pp. 1589-1590, XP002564059 (2000).

Crimi et al., "Purine Derivatives in the Study of Allergic Inflammation in Respiratory Diseases," Allergy, vol. 52, No. 34, pp. 48-54 (1997).

Cristalli et al., "2-Alkynyl Derivatives of Adenosine 5'-N'ethyluronamide: Selective A2 Adenosine Receptor Agonists with Potent Inhibitory Activity on Platelet Aggretation," J. Med. Chem., vol. 37, pp. 1720-1726 (1994).

Cushley et al., "Inhaled Adenosine and Guanosine on Airway Resistance in Normal and Asthmatic Subjects," Br. J. Clin. Pharmacol, vol. 15, No. 2, pp. 161-165 (1983).

Dalpiaz et al., "De Novo Analysis of Receptor Binding Affinity Data of Xanthine Adenosine Receptor Antagonists," Arzneim-Forsch/Drug Res., vol. 45, No. 3, pp. 230-233 (1995).

Dhalla et al., "Tachycardia Caused by A2A Adenosine Receptor Agonists is Mediated by Direct Sympathoexcitation in Awake Rates," Journal of Pharmacology and Experimental Therapeutics, USA, vol. 316, No. 2, pp. 695-702, XP009073100 (2006).

Driver et al., "Adenosine in Bronchoalveolar Lavage Fluid in Asthma," Am. Rev. Respir. Dis., vol. 148, No. 1, pp. 91-97 (1993).

Elias et al., "Airway Remodeling in Asthma," The Journal Of Clinical Investigation, vol. 104, No. 8, pp. 1001-1006 (1999).

Erickson et al., "1,3,8-Trisubstituted Xanthines. Effects of Substitution Pattern upon Adenosine Receptor $A_1/A_2$ Affinity", J. Med. Chem., vol. 34, pp. 1431-1435 (1991).

Feoktistov et al., "Adenosine $A_{2B}$ Receptors: A Novel Therapeutic Target In Asthma," Trends Pharmacol. Sci., vol. 19, pp. 148-153 (1998).

Feoktistov et al., "Hypoxia Modulates Adenosine Receptors in Human Endothelial And Smooth Muscle Cells Toward An A2B Angiogenic Phenotype," Hypertension, vol. 44, No. 5, pp. 649-654, Epub 2004, PMID: 15452028 [PubMed—indexed for MEDLINE] (2004).

Gao et al., "Novel Short-Acting A2A Adenosine Receptor Agonists for Coronary Vasodilation: Inverse Relationship between Affinity and Duration of Action of A2A Agonists," Journal of Pharmacology and Experimental Therapeutics, vol. 298, pp. 209-218 (2001).

Glover et al., "Characterization of a New, Highly Selective Adenosine A2A Receptor Agonist with Potential Use in Pharmacologic Stress Perfusion Imaging", Circulation, vol. 110, pp. I-311 (1999).

Glover et al., "Pharmacological Stress Thallium Scintigraphy with 2-cyclohexylmethylidenehydrazinoadenosine (WRC-0470)," Circulation, vol. 94, pp. 1726-1732 (1996).

Harvey, "Blood Fluids, Electrolytes and Hematologic Drugs," Chapter 40 in Remington's Pharmaceutical Sciences, 18th Ed., Gennaro et al., Mack Publishing Co., East, PA, only pp. 800 and 821 supplied (1990).

Hendel et al. "Initial Clinical Experience with Regadenoson, a Novel Selective A2A Agonist for Pharmacologic Stress Single-Photon Emission Computed Tomography Myocardial Perfusion Imaging", Journal of the American College of Cardiology, vol. 46, No. 11, pp. 2069-2075 (2005).

Hendel et al., "Pharmacologic Stress SPECT Myocardial Perfusion Imaging with a Selective A2A Agonist: Results of a Pilot Study Comparing Adenosine with CVT-3146", Circulation, Supplement IV, vol. 108, pp. 2892 (2003).

Holgate et al., "Roles Of Cysteinyl Leukotrienes In Airway Inflammation, Smooth Muscle Function and Remodeling," J. Allergy Clin. Imunol. (Suppl):S18-34; discussion S34-6, Review, PMID:12532084 [PubMed—indexed for MEDLINE] (2003).

Hoshino, "Impact of Inhaled Corticosteroids and Leukotrience Receptor Antagonists on Airway Remodeling," Clinical Reviews in Allergy & Immunology, vol. 27, No. 1, pp. 59-64 (2004).

Iskandrian, "Adenosine Myocardial Perfusion Imaging," The Journal of Nuclear Medicine, vol. 35, pp. 734-736 (1994).

Jacobson et al., "1,3-Dialkylxanthine Derivatives Having High Potency as Antagonists at Human $A_{2B}$ Adenosine Receptors," Drug Development Research, vol. 47, pp. 45-53 (1999).

Jadbabaie et al., "Myocardial perfusion imaging with a novel selective A2A Adenosine Receptor Agonists (CVT-3146): Important differences in radiotracer behavior," Journal of Am. Col. Cardiology, vol. 41, pp. 443-444 (2003).

Jeffery, "Remodeling in Asthma and Chronic Obstructive Lung Disease," Am. J. Respir. Crit. Care Med., vol. 164, No. 10pt2, pp. S28-S38 (2001).

Katsushima et al., "Structure-Activity Relationships of 8-Cycloalky-1,3-dipropylxanthines as Antagonist of Adenosine Receptors," J. Med. Chem., vol. 33, pp. 1906-1910 (1990).

Kerensky et al. "Dose Dependent Increase in Human Coronary Blood Flow Velocity Following an IV Bolus of CVT-3146, A Novel A2A Adenosine Receptor Agonists: A Potential Agent for the Use in Pharmacological Stress Testing for Myocardial Perfusion Imaging", Circulation, Supplemental II, vol. 106, vol. 19, p. II-618, (2002).

Kim et al., "Acyl-Hydrazide Derivatives of a Xanthine Carboxylic Congener (XCC) as Selective Antagonists at Human $A_{2B}$ Adenosine Receptors", Drug Development Research, vol. 47, pp. 178-188 (1999).

Kleiner, "Reactions of Some 8-(3-Pyridyl)-6-thioxanthines with Methyl Iodide," pp. 739-743 (1973).

Klotz et al., "Comparative pharmacology of human adenosine receptors subtypes—characterization of stably transfected receptors in CHO cells," Nauny-Schmideberg's Arch Pharmacol., vol. 357, pp. 1-9 (1998).

Koepfli et al., "Interaction of caffeine with regadenoson-induced hyperemic myocardial blood flow as measured by PET", European Heart Journal, vol. 27, No. Supp. 1, p. 175, (2006).

Korolkovas, Essentials of Molecular Pharmacology—Background for Drug Design, Wiley—Interscience, New York, NY, only pp. 266-272 supplied, (1970).

Kubo et al., "Effect of Caffeine Intake on Myocardial Hyperemic Flow Induced by Adenosine Triphosphate and Dipyridamole," The Journal of Nuclear Medicine, vol. 45, No. 5, pp. 730-738, (2004).

Leigh et al., "Is Interleukin-1 3 Critical in Maintaining Airway Hyperresponsiveness in Allergen-Challenged Mice?" Am. J. Respir. Crit. Care Med., PMID: 15242841 [PubMed—indexed for MEDLINE] vol. 170, No. 8, pp. 851-856 (2004).

Kusmic et al., "Coronary microcirculatory vasoconstriction induced by low-flow ischemia in mouse hearts is reversed by an A2A adenosine receptor", FASEB Journal, pp. A1227-A1228 (2007).

Linden et al., "Characterization of Human $A_{2B}$ Adenosine Receptors: Radioligand Binding, Western Blotting and Coupling to Gq in Human Embryonic Kidney 293 Cells and HMC-1 Mast Cells," Molecular Pharmacology, vol. 56, pp. 705-713 (1999).

Mager et al., "Molecular Simulation Applied to 2-(N'-alkylidenehydrazino)- and 2-(N'-aralkylidenehydrazino) adenosine A2 Agonists," European Journal of Medicinal Chemistry, vol. 30, pp. 15-25 (1995).

Mann et al., "Airway Effects of Purine Nucleosides and Nucleotides And Release With Bronchial Provocation in Asthma," J. Appl. Physiol., vol. 61, No. 5, pp. 1667-1676 (1986).

Martin et al., "Pharmacology of 2-cylohexylmethylidenehydrazionoadenosine (WRC-0470), a novel, short-acting adenosine A-2A receptor agonist that produces selective coronary vasodilation", Drug Development Research, vol. 40, No. 4, pp. 313-324, (1997).

Martinson et al., "Potent Adenosine Receptor Antagonists that are Selective for the $A_1$ Receptor Subtype," Molecular Pharmacology, vol. 31, No. 3, pp. 247-252 (1986).

Marumoto et al. (I), "Synthesis and Coronary Vasodilating Activity of 2-Substituted Adenosines," Chemical Pharmaceutical Bulletin, vol. 23, No. 4, pp. 759-774 (1975).

Marumoto et al. (II), "Synthesis and Enzymatic Activity of Adenosine 3',5'-Cyclic Phosphate Analogues," Chemical Pharmaceutical Bulletin, vol. 27, No. 4, pp. 990-1003 (1979).

Matsuda et al., "Nucleosides and Nucleotides, 103. 2-Alkynyladenoines: A Novel Class of Selective Adenosine A2 Receptor Agonists with Potent Antihypertensive Effects," Journal of Medicinal Chemistry, vol. 35, No. 1, pp. 241-252 (1992).

Mosselhi et al., "Reactions of some 8-diazoxanthine derivatives", Indian Journal of Chemistry, vol. 33B, pp. 236-242 (1994).

Niiya et al., "2-(N'-Alkylidenehydrazino) Adenosines; Potent and Selective Coronary vasodilators," Journal of Medicinal Chemistry, American Chemical Society, vol. 35, No. 24, pp. 4557-4561, (1992).

Ogden, et al., Mean Body Weight, Height, and Body Mass Index, United States 1960-2002, U.S. National Health and Nutrition Examination Survey, Advance Data No. 347, pp. 1-18, (2004).

Persson et al., "Synthesis and Antiviral Effects of 2-Heteroaryl Substituted Adenosine and 8-Heteroaryl Guanosine Deriviatives," Bioorganic & Medicinal Chemistry, vol. 3, No. 10, pp. 1377-1382 (1995).

Pfizer, "Health info.", (2003), http://www.pfizer.be/English/What_we_do_/Health_info/COPD.htm.

Pifferi et al., "Montelukast and Airway Remodeling in Children with Chronic Persistent Asthma: An Open Study," Pediatric Allergy And Immunology, vol. 15, No. 5, pp. L472-L473 (2004).

Polosa et al., "Evolving Concepts On The Value Of Adenosine Hyperresponsiveness In Asthma And Chronic Obstructive Pulmonary Disease". Thorax, vol. 57, No. 7, pp. 649-654 (2002).

Polosa, "Adenosine-Receptor Subtypes: The Relevance To Adenosine-Mediated Responses In Asthma And Chronic Obstructive Pulmonary Disease," The European Respiratory Journal: Official Journal Of The European Society For Clinical Respiratory Physiology., vol. 20, No. 2, pp. 488-496 (2002).

Riou et al., "Influence of propranolol, enalaprilat, verapamil, and caffeine on adenosine A(2A) receptor medicated coronary vasodilation", Journal of the American College of Cardiology, vol. 40, No. 9, pp. 1687-1690 (2002).

Roth et al., "8-Dicyclopropylmethyl-1,3-dipropylxanthine: A Potent and Selective Adenosine A1 Antagonist with Renal Protective and Diuretic Activities," J. Med. Chem., vol. 34, No. 1, pp. 466-469 (1991).

Ryzhov et al., "Adenosine-Activated Mast Cells Induce IgE Synthesis by B Lymphocytes: An $A_{2B}$-Mediated Process Involving the Cytokines IL-4 and IL-13 with Implications for Asthma," vol. 172, No. 12, pp. 7726-7733, PMID: 15187156 [PubMed—indexed for MEDLINE] (2004).

Shimada et al., "8-Polycycloalkyl-I,3-dipropylxanthines as Potent and Selective Antagonists for A1 -Adenosine Receptors," J. Med. Chem., vol. 35, pp. 924-930 (1992).

Spicuzza et al., "The Role of Adenosine as a Novel Bronchoprovocant in Asthma," Curr. Opin. Allergy Clin. Immunol., vol. 3, No. 1, pp. 65-69 (2003).

Spicuzza et al., "Research Applications and Implications of Adenosine in Diseased Airways," Trends Pharmacol. Sci., vol. 24, No. 8, pp. 409-413, Review, PMID: 12915050 [Pubmed—indexed for MEDLINE] (2003).

Swinyard et al., "Pharmaceutical Necessities," Chapter 66 in Remington's Pharmaceutical Sciences, 18th Ed., Gennaro et al. (eds.), Mack Publishing Co, Easton, PA, only pp. 1318-1319 supplied (1990).

Swinyard et al., "Pharmaceutical Necessities," Chapter 66 in Remington's Pharmaceutical Sciences, 18th Ed., Gennaro et al. (eds.), Mack Publishing Co, Easton, PA, only pp. 1286-1329 supplied (1990).

Tomita et al., Artificial Neural Network Approach for Selection of Susceptible single Nucleotide Polymorphisms and Construction of Prediction Model on Childhood allergic Asthma: BMC Bioinformatics, vol. 1, No. 5, p. 120, PMID: 15339344 [PubMed—indexed for MEDLINE] (2004).

Trochu et al., "Selective A2A Adenosine Receptor Agonist as a Coronary Vasodilator in Conscious Dogs: Potential for Use in Myocardial Perfusion Imaging," Journal of Cardiovascular, vol. 41, No. 1, pp. 132-139 (2003).

Udelson et al., "Randomized, Controlled Dose-Ranging Study of the Selective Adenosine $A_{2A}$ Receptor Agonist Binodenoson for Pharmacological Stress as an Adjunct to Myocardial Perfusion Imaging," Circulation, vol. 209, pp. 457-464 (2004).

Van Der Wenden et al., "Mapping the Xanthine C8-region of the adenosine $A_1$ Receptor with Computer Graphics," European Journal of Pharmacology-Molecular Pharmacology Section, vol. 206, No. 1, pp. 315-323 (1991).

Xu et al., Coronary Vasodilation by a Short Acting, Low Affinity A2A Adenosine Receptor Agonist in Anesthetize Closed Chest Dogs: A Second Generation of Coronary Artery Pharmacologic Stressor, Circulation, vol. 102, No. 18, p. 3912 (2000).

Zhao et al., "Caffeine attenuates the duration of coronary vasodilation and changes in hemodynamics induced by regadenoson (CVT-3146), a novel adenosine A2A receptor agonist," Journal of Cardiovascular Pharmacology, Raven Press, New York, NY, vol. 49, No. 6, pp. 369-375, XP009094871 (2007).

Zhao et al., "Comparative Profile of Vasodilation by CVT-3146, a novel $A_{2A}$ receptor agonist and adenosine in conscious dogs," Journal of Pharm & Experimental Therapeutics, Journal of Pharm. & Experimental Therapeutics, vol. 41, pp. 182-189 (2003).

Zhao et al., "Effects of caffeine on coronary vasodilation and sinue tachycardia induced by Regadenoson, a novel adenosine A2A receptor agonist, in conscious dogs," European Heart Journal, vol. 27, No. Suppl. 1, p. 424 (2006).

Zhao et al., "Regadenoson, a novel pharmacologic stress agent for use in myocardial perfusion imaging, does not have a direct effect on the QT interval in conscious dogs," Journal of Cardio Vascular Pharmacology, pp. 467-473, vol. 52, No. 5, Lippincott Williams and Wilkins, USA, XP8117431 (2008).

Zhong et al., "Synergy Between A2B Adenosine Receptors and Hypoxia in Activating Human Lung Fibroblasts," American Journal of Respiratory Cell and Molecular Biology, vol. 32, No. 1, pp. 2-8 (2005).

Zablocki et al., "2-Substituted PI System Derivatives of Adenosine That Are Coronary Vasodilators Acting Via the A2A Adenosine Receptor," 2001, Nucleosides, Nucleotides and Nucleic Acids, 20(4-7), pp. 343-360.

U.S. Appl. No. 10/896,766, filed on Jul. 22, 2004, Biaggioni, et al.
U.S. Appl. No. 12/637,311, filed on Dec. 14, 2009, Zablocki, et al.
U.S. Appl. No. 12/687,077, filed on Jan. 13, 2010, Zablocki, et al.
U.S. Appl. No. 12/695,096, filed on Jan. 27, 2010, Belardinelli, et al.
U.S. Appl. No. 12/749,328, filed on Mar. 29, 2010, Belardinelli, et al.
PCT/US2009/058850, filed on Sep. 29, 2009, Gilead Palo Alto, Inc.

USE OF $A_{2A}$ ADENOSINE RECEPTOR AGONISTS

This application is a continuation of U.S. patent application Ser. No. 11/253,322, filed Oct. 19, 2005, now U.S. Pat. No. 7,655,636, which claims the benefit under 35 U.S.C. §119(e) of U.S. Provisional Patent Application Ser. No. 60/620,577 filed Oct. 20, 2004, which are hereby incorporated by reference in their entirety.

FIELD OF THE INVENTION

This invention relates to myocardial imaging methods that are accomplished by administering doses of regadenoson—an adenosine $A_{2A}$ receptor agonist—to a mammal undergoing myocardial imaging.

DESCRIPTION OF THE ART

Myocardial perfusion imaging (MPI) is a diagnostic technique useful for the detection and characterization of coronary artery disease. Perfusion imaging uses materials such as radionuclides to identify areas of insufficient blood flow. In MPI, blood flow is measured at rest, and the result compared with the blood flow measured during exercise on a treadmill (cardiac stress testing), such exertion being necessary to stimulate blood flow. Unfortunately, many patients are unable to exercise at levels necessary to provide sufficient blood flow, due to medical conditions such as peripheral vascular disease, arthritis, and the like.

Therefore, a pharmacological agent that increases cardiac blood flow (CBF) for a short period of time would be of great benefit, particularly one that did not cause peripheral vasodilation. Vasodilators, for example dipyridamole, have been used for this purpose in patients prior to imaging with radionuclide. Dipyridamole is a long-acting compound and frequently requires antidotes to reverse the prolonged side effects. It is an infusion rather than a bolus (like regadenoson). It is also non-selective for adenosine receptors and requires weight-based dosing.

Adenosine, a naturally occurring nucleoside, also is useful as a vasodilator. Adenosine exerts its biological effects by interacting with a family of adenosine receptors characterized as subtypes $A_1$, $A_{2A}$, $A_{2B}$, and $A_3$. Adenoscan® is a formulation of a naturally occurring adenosine. Adenoscan® has been marketed as an adjuvant in perfusion studies using radioactive thallium-201. However, its use is limited due to side effects such as flushing, chest discomfort, the urge to breathe deeply, headache, throat, neck, and jaw pain. These adverse effects of adenosine are due to the activation of other adenosine receptor subtypes other than $A_{2A}$, which mediates peripheral vasodilatory effects to bronchoconstriction of adenosine. Additionally, the short half-life of adenosine necessitates continuous infusion during the procedure, further complicating its use. Adenoscan® is contraindicated in many patients including those with second- or third-degree block, sinus node disease, bronchoconstrictive or bronchospastic lung disease, and in patients with known hypersensitivity to the drug.

Other potent and selective agonists for the $A_{2A}$ adenosine receptor are known. For example, MRE-0470 (Medco) is an adenosine $A_{2A}$ receptor agonist that is a potent and selective derivative of adenosine. WRC-0470 (Medco) is an adenosine $A_{2A}$ agonist used as an adjuvant in imaging. In general, compounds such as these have a high affinity for the $A_{2A}$ receptor, and consequently, a long duration of action, which is undesirable in imaging, and could possibly prolong the duration of side effects.

One especially potent and useful adenosine $A_{2A}$ receptor agonist is regadenoson. Regadenoson is selective for the adenosine $A_{2A}$ receptor, has a short duration of action and does not appear to require administration as a continuous infusion. Regadenoson and related compounds as well as methods for their manufacture and use in cardiac perfusion imagining are disclosed in U.S. Pat. Nos. 6,403,567, 6,642,210, 6,214,807, and 6,770,634, as well as in published U.S. patent application nos. 2002-0012946 and 2004-0022177 the entirety of each specification of which are incorporated herein by reference. Although regadenoson is a known compound, much remains unknown about its pharmacokinetic profile and range of potential therapeutic uses.

SUMMARY OF THE INVENTION

One aspect of this invention is a method of producing coronary vasodilation with little peripheral vasodilation comprising administering to a human a single dose of a pharmaceutical composition comprising regadenoson and at least one pharmaceutical excipient in an amount that is sufficient to increase the average coronary peak flow velocity by at least about 16.5 cm/sec.

Another aspect of this invention is a method of producing coronary vasodilation with little peripheral vasodilation comprising administering to a human a single dose of a pharmaceutical composition comprising regadenoson and at least one pharmaceutical to excipient in an amount that is sufficient to increase the average coronary peak flow velocity by at least about 16.5 cm/sec wherein the pharmaceutical composition is administered by iv bolus.

Yet another aspect of this invention is a method of producing coronary vasodilation with little peripheral vasodilation comprising administering to a human a single dose of a pharmaceutical composition comprising regadenoson and at least one pharmaceutical excipient in an amount that is sufficient to increase the average coronary peak flow velocity by at least about 16.5 cm/sec wherein the pharmaceutical composition is administered in about 10 to about 20 seconds.

Still another aspect of this invention is a method of producing coronary vasodilation with little peripheral vasodilation comprising administering to a human a single dose of a pharmaceutical composition comprising regadenoson and at least one pharmaceutical excipient in an amount that is sufficient to increase the average coronary peak flow velocity by at least about 16.5 cm/sec wherein the amount of the pharmaceutical composition administered is sufficient to raise the average coronary peak flow velocity by an amount ranging from about 16.5 to about 77.0 cm/sec.

In still another aspect of this invention the single dose of pharmaceutical composition includes from about 10 to about 500 micrograms of regadenoson or alternatively includes an amount of regadenoson ranging from about 0.05 to about 60 µg/kg weight of the human.

In yet another aspect, this invention includes the step of performing myocardial perfusion imaging of the human following the administration of the single dose of the pharmaceutical composition to the human. In this aspect of the invention, at least one radionuclide may be administered to the human at a time selected from the group consisting of before the human receives the dose of pharmaceutical composition, simultaneously with the administration of the dose of pharmaceutical composition or is after administering the dose of pharmaceutical composition to the human. This means the radionuclide and the single dose of the pharmaceutical composition may be administered separately to the human or simultaneously to the human. In a preferred aspect of this method, myocardium examination begins no sooner than about 1 minute after the single dose of the pharmaceutical composition is administered to the human.

DESCRIPTION OF A PREFERRED EMBODIMENT

Potent $A_{2A}$ agonists are useful as adjuncts in cardiac imaging when added either prior to dosing with an imaging agent or simultaneously with an imaging agent. Suitable imaging agents include, but are not limited to $^{201}$Thallium or $^{99m}$Technetium-Sestamibi, $^{99m}$Tc-teboroxime, and Technetium-99m (III).

New and potent $A_{2A}$ agonists that increase CBF but do not significantly increase peripheral blood flow have been identified. One particularly useful $A_{2A}$ agonists is regadenoson. Regadenoson is also referred to in the literature as CVT-3146 or (1-{9-[(4S,2R,3R,5R)-3,4-dihydroxy-5-(hydroxymethyl)oxolan-2-yl]-6-aminopurin-2-yl}pyrazol-4-yl)-N-methyl-carboxamide and has the formula:

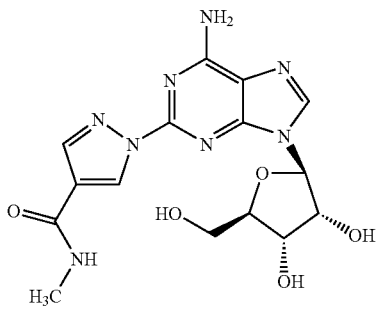

Methods for synthesizing regadenoson and related compounds are set forth in U.S. Pat. No. 6,403,567, the specification of which is incorporated herein by reference in its entirety.

Regadenoson may be administered by pharmaceutical administration methods that are known in the art. It is preferred that regadenoson is dosed i.v. It is more preferred that regadenoson is administered in a single dose i.v. The term "single dose" refers generally to a single quickly administered dose of a therapeutic amount of regadenoson. The term "single dose" does not encompass a dose or doses administered over an extended period of time by, for example continuous i.v. infusion.

Regadenoson will typically be incorporated into a pharmaceutical composition prior to use. The term "pharmaceutical composition" refers to the combination of regadenoson with at least one liquid carrier that together form a solution or a suspension. Lyophilized powders including compositions of this invention fall within the scope of "pharmaceutical compositions" so long as the powders are intended to be reconstituted by the addition of a suitable liquid carrier prior to use. Examples of suitable liquid carriers include, but are not limited to water, distilled water, de-ionized water, saline, buffer solutions, normal isotonic saline solution, dextrose in water, and combinations thereof. Such pharmaceutical compositions are generally suitable for injection.

The term "buffer solution" or "buffer" as used herein refers to a solution containing both a weak acid and its conjugate weak base. The buffer solutions are used in pharmaceutical compositions of this invention in order to resist pH changes. Non-limiting examples of useful buffer solutions are solutions that comprise sodium bicarbonate and sodium phosphate.

Pharmaceutical compounds including the compounds of this invention, and/or derivatives thereof, may be formulated as solutions or lyophilized powders for parenteral administration. Powders may be reconstituted by addition of a suitable diluent or other pharmaceutically acceptable carrier prior to use. If used in liquid form the compounds of this invention are preferably incorporated into a buffered, isotonic, aqueous solution. Examples of suitable diluents are normal isotonic saline solution, standard 5% dextrose in water and buffered sodium or ammonium acetate solution. Such liquid formulations are suitable for parenteral administration, but may also be used for oral administration. It may be desirable to add excipients such as polyvinylpyrrolidinone, gelatin, hydroxy cellulose, acacia, polyethylene glycol, mannitol, sodium chloride, sodium citrate or any other excipient known to one of skill in the art to pharmaceutical compositions including compounds of this invention.

Pharmaceutical compositions including regadenoson may be prepared and then administered, with or without intervening storage. Various properties considered when formulating pharmaceutical compositions of this invention include, but are not limited to product shelf life, regadenoson solubility, composition pH, vein irritation, hemolysis, storage conditions (e.g., whether the pharmaceutical composition will be stored at room temperature or some other temperature) and the ability to withstand sterilization procedures.

One method to achieve the desired pharmaceutical composition properties is to include a co-solvent in the pharmaceutical composition. The co-solvent can be selected from any liquid or compound in solution that imparts the desired properties to the pharmaceutical composition. Examples of useful co-solvents include, but are not limited to methylboronic acid, borate buffer, propylene glycol, or polyethylene glycol. The amount of co-solvent in the pharmaceutical composition will depend upon properties, such as solubility and stability of the chosen $A_{2A}$ receptor agonist. Examples of pharmaceutical compositions containing co-solvents can be found in U.S. Patent Publication No. 2005/0020915, the specification of which is incorporated herein by reference in its entirety.

Regadenoson has solubility in water of about 50 micrograms/mL. Therefore, regadenoson can be dissolved and administered in water so long as the desired weight amount of regadenoson can be administered in an acceptable volume. For example, a preferred dose of about 400 micrograms can be administered in 8 mL of water. If this volume is too great for administration purposes, or if the pharmaceutical composition will be stored at other than room temperature (RT), then additional ingredients can be added to the composition to increase the solubility of regadenoson in the composition and/or to provide the resulting pharmaceutical composition with other improved properties such as improved stability and storage properties.

Pharmaceutical compositions of this invention that include regadenoson may include up to about 1 milligram/mL of regadenoson. It is preferred that pharmaceutical compositions including regadenoson include from about 50 to about 250 micrograms/mL, and more preferably from about 50 to 150 micrograms/mL of regadenoson.

In order to improve solubility and storage properties, regadenoson can be administered in a pharmaceutical composition including a methylboronic acid (MBA) co-solvent. The methylboronic acid is added to the pharmaceutical composition to improve agonist solubility and shelf life. MBA increases the pH of the resulting composition. The solubility of regadenoson in a pharmaceutical composition including MBA tends to decrease as the composition pH drops towards neutral. Therefore, with regadenoson, an optimal MBA-containing composition pH is from about 8.5 to 10 with a pH of about 9.1 to about 9.4 being preferred and a pH of about 9.3 being most preferred. This corresponds to a composition including from about 50 to about 250 mg/mL of MBA. As an alternative to MBA, regadenoson can be combined with a borate buffer solution. Typically, a borate buffer solution will be comprised of an aqueous solution of sodium borate that is adjusted to the desired pH such as a pH of 9.3 using an acid or a base.

MBA containing pharmaceutical compositions can suffer from storage problems. Namely, MBA can cause delamination when packaged in certain type I glass vessels. This problem can be overcome by storing the MBA containing pharmaceutical compositions in plastic vessels or in more resistant type I glass vessels.

If regadenoson containing pharmaceutical compositions having a pH closer to neutral are desired, then an alternative is to combine regadenoson with a propylene glycol (PG) co-solvent. The amount of PG used in the composition may range from about 5% to up to 25% by volume with a range of about 8% to about 20% by volume being more preferred when using regadenoson. An alternative to PG is polyethylene glycol—PEG. A preferred PEG will have an average molecular weight of from about 200 to 400.

Preferably, the regadenoson composition including PG or PEG will have a pH of from about 6 to about 8 with a pH of about 7 being preferred. Any physiologically acceptable buffer capable of adjusting the composition pH to the desired value can be used. Examples of such buffer include, but are not limited to, dibasic sodium phosphate, dibasic sodium phosphate dehydrate, and monobasic sodium phosphate monohydrate. Additional optional ingredients such as EDTA and dimethylacetamide could be employed in the composition as well.

The pharmaceutical compositions of this invention may include one or more anti-oxidants such as butylated hydroxyanisole (BHA).

Regadenoson has a rapid onset of action and a short duration of action when administered. Regadenoson is very useful when administered in a very small quantity in a single bolus intravenous (i.v.) injection. Regadenoson can be administered in amounts as little as 10 µg and as high as 2000 µg or more. An optimal dose may include as little as 10 µg and as much as about 1000 µg or more of regadenoson. More preferably, an optimal dose will range from about 100 to about 500 µg of regadenoson.

It is preferred that regadenoson is administered in a single bolus injection in an amount selected from about 300 µg, about 400 µg, about 500 µg, about 600 µg, and is about 700 µg. These amounts are unexpectedly small when compared with adenosine which is typically administered continuously by IV infusion at a rate of about 140 µg/kg/min. Unlike adenosine, the same dosage of regadenoson can be administered to a human patient regardless of the patient's weight. Thus, the administration of a single uniform amount of regadenoson by iv bolus for myocardial imaging is dramatically simpler and less error prone than the time and weight dependent administration of adenosine. The dose of regadenoson administered to a human patient can, however, be determined by weight. Typically, a weight based dose will range from about 0.05 to about 60 µg/kg and more preferably from about 0.1 to about 30 µg/kg. Regadenoson in particular is generally well tolerated when administered in an amount up to 10 µg/kg in standing patients and up to 20 µg/kg in supine patients.

In an alternative embodiment, regadenoson may be administered orally, intravenously, through the epidermis or by any other means known in the art for administering therapeutic agents with bolus i.v. administration being preferred. In one embodiment, the bolus dosing occurs in 60 seconds or less. In yet other embodiments, the bolus dosing occurs in about 30 seconds or less, and more preferably in about 20 seconds or less or in about 10 seconds or less.

The pharmacokinetics of regadenoson are disclosed in more detail in the following examples.

Example 1

The purpose of this study was to investigate the pharmacokinetics (PK), pharmacodynamics (PD), and the maximum tolerated dose of regadenoson in healthy human subjects.

Thirty-six healthy, male subjects were included in the study. Subjects received single, IV bolus doses of regadenoson ranging from 0.1 to 30 µg/kg. The regadenoson dosage administered in this example and in Examples 2 & 3 below was a neutral pH dose including the preferred ingredients discussed above. Concentrations of regadenoson were determined in plasma samples collected at various times and in urine samples collected over a 24-hour period after drug administration. ECG, blood pressure (BP), and heart rate (HR) were recorded for up to 24 hours post-dose. Adverse events (AE) were monitored for 24 hours post dose and via telephone 7 days later. A population approach was utilized in applying a three-compartmental PK model to the plasma concentration-time and a Michaelis-Menten model to the time-course of heart rate. The potential influence of various covariates on PK and PD model parameters was investigated.

The population value of clearance (CL) was estimated to be 40.6 Uh, with renal clearance accounting for 57% of the total clearance. The volume of distribution of regadenoson was estimated to be 83.3 L. The model estimated a baseline and a maximal increase in HR of 62 and 76 bpm. The concentration of regadenoson causing half-maximal increase in HR (potency) was estimated to be 12.4 ng/mL. Covariates such as, body mass index, body weight, age, and height had no influence on the PK or PD parameters. Adverse events were generally mild to moderate, of rapid onset, short duration, and none required medical intervention. They included abdominal discomfort, chest pressure/tightness, dizziness, dyspnea, flushing, headache, hyperventilation, nausea, palpitations, and vomiting, and increased with dose level. The maximum tolerated dose was 20 µg/kg in the supine position and 10 µg/kg in the standing position, with dose-limiting syncope or near syncope observed in subjects in the standing position.

This example demonstrates that regadenoson is well tolerated in healthy male subjects. The lack of any significant influence of the covariates on the PK and PD model parameters suggests a unit-based dosing for regadenoson.

Example 2

The purpose of this study was to investigate the pharmacokinetics (PK) and pharmacodynamics (PD) of regadenoson in subjects undergoing clinically indicated cardiac catheterization.

Thirty-six male and female subjects undergoing clinically indicated coronary angiography were studied. Subjects received single, IV bolus doses of regadenoson ranging from 10 to 500 µg. Concentrations of regadenoson were determined in plasma samples collected at various times prior to and after drug administration. ECG, average coronary peak flow velocity (APV), measured using intracoronary Doppler flow wire, blood pressure (BP), and heart rate (HR) were continuously monitored for up to 3 hours post-dose. Occurrence of adverse events (AEs) was monitored for approximately 3 hours post dosing and via telephone approximately 14 days later. A population approach was utilized in applying PK and PD models to the plasma concentration, APV, and HR data. The potential influence of various covariates on PK and PD model parameters was investigated.

The PK data were best described by a three-compartment model. The population value of clearance and volume of distribution were estimated to be 29.9 L/h and 68.1 L, respectively. The PD model of the APV data included a hypothetical effect compartment. The baseline and the maximal increase in APV were estimated—based upon this data—to be 16.5 and 105 cm/seconds, with a potency (concentration of regadenoson that causes half maximal effect) of 29.9 ng/mL. The model estimated a small value for the distribution rate constant (4 min$^{-1}$) from the plasma to the effect site, indicating a rather rapid onset of effect. A Michaelis-Menten model resulted in the best fit of the HR data, with estimates of 67 and 41 bpm for the baseline and maximum increase in the HR, and a potency of 27.5 ng/mL. Covariates such as body mass index, body weight, age, and height had no significant influence on the PK or PD parameters. AEs were reported for fewer than half (n=17) of the subjects; events reported for 3 or more subjects were chest discomfort (n=3), tachycardia (n=4), and bleeding at the catheter site (n=3).

These results demonstrate that regadenoson is a potent and well-tolerated coronary vasodilator. The lack of any significant influence of the covariates on the PK and PD model parameters suggests a unit-based dosing for regadenoson.

Example 3

Regadenoson is a selective $A_2$-adenosine receptor agonist under development for acute dilation of the coronary arterial vasculature during myocardial perfusion imaging. $A_{2A}$-adenosine receptor activation is reported to cause inhibition of platelet aggregation and neutrophil activation.

To characterize the drug more completely, in this study, we determined affinity and potency values for binding and for functional responses to regadenoson in preparations of human platelets and neutrophils (membranes and intact cells), CHO cells expressing human $A_{2A}$ receptors (membranes and intact cells), and rat brain striatal membranes. For comparison, parallel assays of responses to the reference $A_{2A}$ agonist CGS21680 were performed alongside each assay of regadenoson. Assay results are reported in Table 1 below.

TABLE 1

Values (mean ± SE) of affinity [Ki] and potency [$EC_{50}$ or $IC_{50}$] for regadenoson at $A_{2A}$-adenosine receptors

| Assay | Preparation | | | |
|---|---|---|---|---|
| | Human platelets | Human neutrophils | CHO hisA$_{2A}$-expressing | Rat striatum |
| Membrane Binding[1] | 534 ± 30 | 327 ± 14 | 347 ± 7 | 318 ± 5 |
| Membrane Binding[2] | | | 50 ± 4 | 43 ± 3 |
| Cell cAMP Content | 472 ± 17 | 406 ± 25 | 56 ± 4 | |
| Platelet Aggregation | 437 ± 44 | | | |

TABLE 1-continued

Values (mean ± SE) of affinity [Ki] and potency [$EC_{50}$ or $IC_{50}$] for regadenoson at $A_{2A}$-adenosine receptors

| Assay | Preparation | | | |
|---|---|---|---|---|
| | Human platelets | Human neutrophils | CHO hisA$_{2A}$-expressing | Rat striatum |
| Cell calcium Mobilization | 108 ± 8 | | | |
| Superoxide anion Production | | 328 ± 32 | | |

[1]displacement of binding of [3H]-ZM241385
[2]displacement of binding of [3H]-CG-S21680

Responses to regadenoson and to CGS21680 were similar in magnitude. In all assays, CGS21680 was slightly more potent than regadenoson (i.e., values of $EC_{50}$ for the 12 assays were 13-fold lower for CGS 21680, on average). It can be concluded from this study that regadenoson, like CGS21680, is not only a coronary vasodilator, but is also an inhibitor of both platelet aggregation and neutrophil activation (i.e., inflammation).

What is claimed is:

1. A method of producing coronary vasodilation in a human in need thereof comprising administering to the human a single intravenous (iv) bolus dose of a pharmaceutical composition comprising:
    a) regadenoson, a compound named (1-{9-[(2R,3R,4S,5R)-3,4-dihydroxy-5-(hydroxymethyl)oxolan-2-yl]-6-aminopurin-2-yl}pyrazol-4-yl)-N-methylcarboxamide, which has the formula:

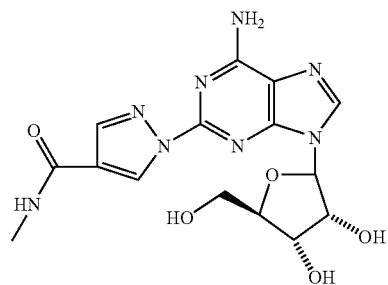

and
    b) at least one pharmaceutical excipient wherein the composition has a pH of from about 6 to about 8;
    wherein the single dose of the pharmaceutical composition is administered in an amount that is sufficient to increase the average coronary peak flow velocity by at least about 16.5 cm/sec to about 105 cm/sec.

2. The method of claim 1, wherein the single dose of the pharmaceutical composition further comprises a member selected from the group consisting of water, distilled water, de-ionized water, saline, buffer solutions, normal isotonic saline solution, dextrose in water, and combinations thereof.

3. The method of claim 2, wherein the single dose of the pharmaceutical composition further comprises a buffer solution and the buffer is selected from the group consisting of dibasic sodium phosphate, dibasic sodium phosphate dehydrate, monobasic sodium phosphate monohydrate, and combinations thereof.

4. The method of claim 3, wherein the buffer is dibasic sodium phosphate and monobasic sodium phosphate monohydrate.

5. The method of claim 4, wherein the single dose of the pharmaceutical composition further comprises EDTA.

6. The method of claim 5, wherein the single dose of the pharmaceutical composition further comprises propylene glycol in an amount from about 5% to about 25% (w:v).

7. The method of claim 6, wherein the propylene glycol is present in an amount from about 8% to about 20% (w:v).

8. The method of claim 7, wherein the single dose of the pharmaceutical composition comprises from about 10 to about 500 micrograms of regadenoson.

9. The method of claim 8, wherein the single dose of the pharmaceutical composition comprises from about 0.05 to about 60 µg/kg of regadenoson.

10. The method of claim 1, wherein the single dose of the pharmaceutical composition is administered in about 10 to about 20 seconds.

11. The method of claim 1, wherein the amount of the single dose of the pharmaceutical composition is sufficient to raise the average coronary peak flow velocity by an amount ranging from about 16.5 to about 77.0 cm/sec.

12. A method of performing myocardial perfusion imaging of a human in need thereof, said method comprising:
   1) administering to the human a single intravenous (iv) bolus dose of a pharmaceutical composition comprising:
      a) regadenoson, a compound named (1-{9-[(2R,3R,4S,5R)-3,4-dihydroxy-5-(hydroxymethyl)oxolan-2-yl]-6-aminopurin-2-yl}pyrazol-4-yl)-N-methylcarboxamide, which has the formula:

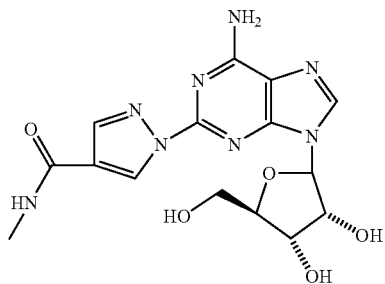

and
      b) at least one pharmaceutical excipient wherein the composition has a pH of from about 6 to about 8;
      wherein the single dose of the pharmaceutical composition is administered in an amount that is sufficient to increase the average coronary peak flow velocity by at least about 16.5 cm/sec to about 105 cm/sec;
   2) administering at least one radionuclide; and
   3) imaging the myocardium of the human, wherein said imaging is conducted at least concomitantly with process steps 1 and 2.

13. The method of claim 12, wherein the single dose of the pharmaceutical composition and the radionuclide are administered to the human simultaneously.

14. The method of claim 12, wherein the single dose of the pharmaceutical composition and the radionuclide are administered to the human separately.

15. The method of claim 12, wherein the myocardium imaging begins no sooner than about 1 minute from the time the single dose of the pharmaceutical composition is administered to the human.

* * * * *